US00PP23051P2

(12) United States Plant Patent
Takahashi

(10) Patent No.: US PP23,051 P2
(45) Date of Patent: Sep. 18, 2012

(54) *VERBENA* PLANT NAMED 'AKIV571-1'

(50) Latin Name: *Verbena hybrida*
Varietal Denomination: AKIV571-1

(75) Inventor: Akiko Takahashi, Gifu (JP)

(73) Assignee: Innovaplant GmbH & Co. KG, Gensingen (DE)

( * ) Notice: Subject to any disclaimer, the term of this patent is extended or adjusted under 35 U.S.C. 154(b) by 280 days.

(21) Appl. No.: 12/802,241

(22) Filed: Jun. 1, 2010

(51) Int. Cl.
*A01H 5/00* (2006.01)

(52) U.S. Cl. ..... Plt./308

(58) Field of Classification Search ..... Plt./308
See application file for complete search history.

(56) References Cited

U.S. PATENT DOCUMENTS

PP14,853 P2 * 6/2004 Sakazaki ..... Plt./308
PP15,604 P2 * 3/2005 Hanes ..... Plt./308
PP16,065 P2 * 10/2005 Sakazaki ..... Plt./308

OTHER PUBLICATIONS

UPOV ROM GTITM Computer Database, GTI Jouve Retrieval Software 2011/04 Citation for 'AKIV571-1'.*
Erischele, Chris. "2011 Superbena Royale Chambray Among Best *Verbena* Annual Flowers." http://chris-erischele.suite101.com Sep. 14, 2010.*
Anonymous. "Superbena *Verbena* hybrids" by Proven Winners accessed online May 1, 2012.*

* cited by examiner

*Primary Examiner* — Wendy C Haas
(74) *Attorney, Agent, or Firm* — C. A. Whealy

(57) ABSTRACT

A new and distinct cultivar of *Verbena* plant named 'AKIV571-1', characterized by its compact, semi-upright, mounding to trailing plant habit; vigorous growth habit; freely branching habit; freely flowering habit; violet-colored flowers that are held above and beyond the foliar plane; and resistance to Powdery Mildew.

1 Drawing Sheet

Botanical designation: *Verbena hybrida.*
Cultivar denomination: 'AKIV571-1'.

BACKGROUND OF THE INVENTION

The present invention relates to a new and distinct cultivar of *Verbena* plant, botanically known as *Verbena hybrida*, and hereinafter referred to by the name 'AKIV571-1'.

The new *Verbena* plant is a product of a planned breeding program conducted by the Inventor in Shiga, Japan and Bonsall, Calif. The objective of the breeding program is to create new compact *Verbena* plants with numerous flowers and resistance to Powdery Mildew.

The new *Verbena* plant originated from a cross-pollination made by the Inventor on May 14, 2007 in Shiga, Japan of a proprietary seedling selection of *Verbena hybrida* identified as code number 07V424-03, not patented, as the female, or seed, parent with a proprietary seedling selection of *Verbena hybrida* identified as 'Nioimurasaki', not patented, as the male, or pollen, parent. The new *Verbena* plant was discovered and selected by the Inventor as a single flowering plant within the progeny of the stated cross-pollination in a controlled environment in Bonsall, Calif. on Jun. 11, 2008.

Asexual reproduction of the new *Verbena* plant by terminal cuttings in a controlled environment in Bonsall, Calif. since Jun. 12, 2008 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'AKIV571-1'. These characteristics in combination distinguish 'AKIV571-1' as a new and distinct *Verbena* plant:

1. Compact, semi-upright, mounding to trailing plant habit.
2. Vigorous growth habit.
3. Freely branching habit.
4. Freely flowering habit.
5. Violet-colored flowers that are held above and beyond the foliar plane.
6. Resistant to Powdery Mildew.

Plants of the new *Verbena* can be compared to plants of the female parent selection. Plants of the new *Verbena* differ primarily from plants of the female parent selection in the following characteristics:

1. Plants of the new *Verbena* are more compact than plants of the female parent selection.
2. Plants of the new *Verbena* have shorter internodes than plants of the female parent selection.
3. Plants of the new *Verbena* have smaller flowers than plants of the female parent selection.
4. Plants of the new *Verbena* and the female parent selection differ in flower color as plants of the female parent selection have pale pink-colored flowers.

Plants of the new *Verbena* can be compared to plants of the male parent selection. Plants of the new *Verbena* differ primarily from plants of the male parent selection in the following characteristics:

1. Plants of the new *Verbena* are more upright than plants of the male parent selection.
2. Plants of the new *Verbena* have larger leaves than plants of the male parent selection.
3. Plants of the new *Verbena* have larger flowers than plants of the male parent selection.

Plants of the new *Verbena* can be compared to plants of the *Verbena hybrida* 'USBENAL8', disclosed in U.S. Plant Pat. No. 14,853. In side-by-side comparisons conducted in Bonsall, Calif., plants of the new *Verbena* differed primarily from plants of 'USBENAL8' in the following characteristics:

1. Plants of the new *Verbena* were more compact than plants of 'USBENAL8'.
2. Plants of the new *Verbena* were more freely branching than plants of 'USBENAL8'.
3. Plants of the new *Verbena* had narrower leaves than plants of 'USBENAL8'.
4. Plants of the new *Verbena* had smaller flowers than plants of 'USBENAL8'.

Plants of the new *Verbena* can also be compared to plants of the *Verbena hybrida* 'Lan Bule', disclosed in U.S. Plant Pat. No. 15,604. In side-by-side comparisons conducted in Bonsall, Calif., plants of the new *Verbena* differed primarily from plants of 'Lan Bule' in the following characteristics:

1. Plants of the new *Verbena* had smaller flowers than plants of 'Lan Bule'.
2. Plants of the new *Verbena* and 'Lan Bule' differed in flower color as plants of 'Lan Bule' had dark blue violet-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'AKIV571-1' grown in a container.

The photograph at the top of the sheet is a close-up view of a typical flowering plant of 'AKIV571-1'.

DETAILED BOTANICAL DESCRIPTION

Plants used for the aforementioned photographs and following description were grown under conditions which closely approximate commercial production conditions during the spring in 15-cm containers in a polyethylene-covered greenhouse in Bonsall, Calif. During the production of the plants, day temperatures ranged from 18° C. to 32° C., night temperatures ranged from 14° C. to 18° C. and light levels ranged from 7,000 to 10,000 foot-candles. Plants were pinched one time and were nine weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'AKIV571-1'.

Parentage:

*Female, or seed, parent*.—Proprietary seedling selection of *Verbena hybrida* identified as code number 07V424-03, not patented.

*Male, or pollen, parent*.—Proprietary seedling selection of *Verbena hybrida* identified as 'Nioimurasaki', not patented.

Propagation:

*Type cutting*.—Vegetative tip cuttings.

*Time to initiate roots, summer*.—About three days at temperatures ranging from 17° C. to 29° C.

*Time to initiate roots, winter*.—About four days at temperatures ranging from 17° C. to 21° C.

*Time to produce a rooted plant, summer*.—About 15 days at temperatures ranging from 17° C. to 29° C.

*Time to produce a rooted plant, winter*.—About 20 days at temperatures ranging from 17° C. to 21° C.

*Root description*.—Medium in thickness, fibrous; white in color.

*Rooting habit*.—Freely branching; medium in density.

Plant description:

*Plant and growth habit*.—Compact, semi-upright, mounding to trailing plant habit; freely branching habit with about six primary lateral branches developing per plant each with numerous secondary branches; pinching enhances lateral branch development; dense and bushy plant habit; vigorous growth habit.

*Plant height*.—About 10.5 cm.

*Plant diameter* (*spread*).—About 49 cm by 53 cm.

Lateral branch description:

*Length*.—About 31 cm.

*Diameter*.—About 2.5 mm.

*Internode length*.—About 3 cm.

*Orientation*.—Initially upright then outwardly spreading.

*Strength*.—Strong.

*Texture*.—Pubescent.

*Color*.—Close to 146A.

Foliage description:

*Arrangement*.—Opposite, simple.

*Length*.—About 3.4 cm.

*Width*.—About 2.2 cm.

*Shape*.—Oblong to elliptical.

*Apex*.—Broadly acute.

*Base*.—Truncate.

*Margin*.—Irregularly crenate.

*Texture, upper and lower surfaces*.—Pubescent.

*Venation pattern*.—Pinnate; reticulate.

*Color*.—Developing leaves, upper surface: Close to 137A. Developing leaves, lower surface: Close to N138B. Fully expanded leaves, upper surface: Close to N137B; venation, close to 137B. Fully expanded leaves, lower surface: Close to 147B; venation, close to 148C.

*Petiole*.—Length: About 5 mm. Diameter: About 2 mm. Texture, upper and lower surfaces: Pubescent. Color, upper and lower surfaces: Close to 147C.

Flower description:

*Flower arrangement and habit*.—Salverform sessile flowers arranged in compact hemispherical terminal racemes; flowers face upward or outward; freely flowering habit with about 30 flowers per inflorescence.

*Natural flowering season*.—Plants flower continuously from spring through the autumn in California; plants begin flowering about six weeks after planting.

*Flower longevity*.—Flowers last about five to seven days on the plant; flowers not persistent.

*Fragrance*.—None detected.

*Inflorescence height*.—About 3 cm.

*Inflorescence diameter*.—About 4.3 cm.

*Flower diameter*.—About 1.4 cm.

*Flower depth* (*height*).—About 2.8 cm.

*Throat diameter*.—About 2 mm.

*Tube length*.—About 1.8 cm.

*Tube diameter, proximal*.—About 1.5 mm.

*Flower buds*.—Length: About 1.8 cm. Diameter: About 5 mm. Shape: Elongated oblong. Color: Close to N88A.

*Corolla*.—Arrangement: Single whorl of five fused petals fused towards the base into a narrow tube. Petal lobe length: About 7 mm. Petal lobe width: About 5 mm. Petal lobe shape: Roughly cordate. Petal lobe apex: Emarginate to cordate. Petal margin: Entire. Petal texture, upper and lower surfaces: Smooth, glabrous; velvety. Color: Petal, when opening, upper surface: Close to N89A. Petal, when opening, lower surface: Close to 90A. Petal, fully opened, upper surface: Close to 86B; with development, color becoming closer to 86C with close to 91A to 91B towards the base. Petal, fully opened, lower surface: Close to 90A; does not fade with development. Throat: Close to 145D. Tube: Close to 92B to 92C.

*Calyx*.—Arrangement: Single whorl of five fused sepals fused towards the base into a narrow tube. Sepal length: About 1 cm. Sepal width: About 1 mm. Sepal shape: Narrowly lanceolate. Sepal apex: Acute. Sepal margin: Entire. Sepal texture, upper surface: Smooth, glabrous. Sepal texture, lower surface: Pubescent. Sepal color, upper and lower surfaces: Close to 146A.

*Peduncles*.—Length: About 6.5 cm. Diameter: About 2 mm. Strength: Strong. Texture: Pubescent. Color: Close to 146B.

*Reproductive organs*.—Stamens: Quantity/arrangement: Four per flower, filaments are adnate to corolla tube. Filament length: About 1 mm. Filament color: Close to 145C. Anther shape: Oval, bi-lobed. Anther length: About 1 mm. Anther color: Close to 153A. Pollen amount: Scarce. Pollen color: Close to N144A. Pistils: Quantity: One per flower. Pistil length: About 1.8 cm. Stigma shape: Rounded, bi-parted. Stigma color: Close to 144A. Style length: About 1.5 cm. Style color: Close to N145A to N145B. Ovary color: Close to 144A. Fruits/seed: Fruit and seed development have not been observed on plants of the new *Verbena*.

Temperature tolerance: Plants of the new *Verbena* have been observed to tolerate temperatures from about 1° C. to about 46° C.

Pathogen/pest resistance: Plants of the new *Verbena* have been observed to be tolerant to Powdery Mildew. Plants of the new *Verbena* have not been observed to be resistant to pests and other pathogens common to *Verbena* plants.

It is claimed:

1. A new and distinct *Verbena* plant named 'AKIV571-1' as illustrated and described.

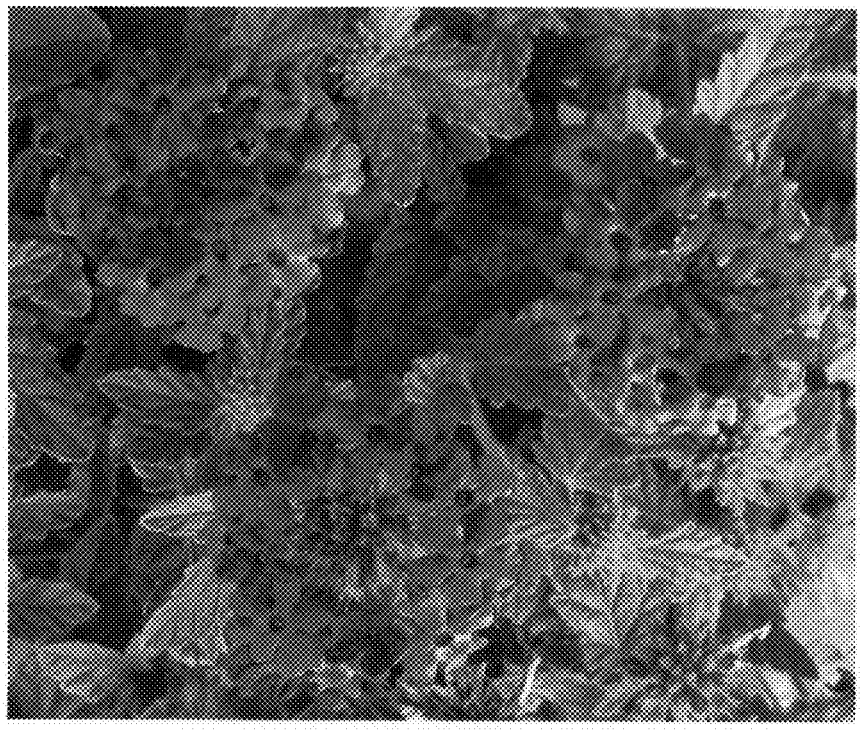
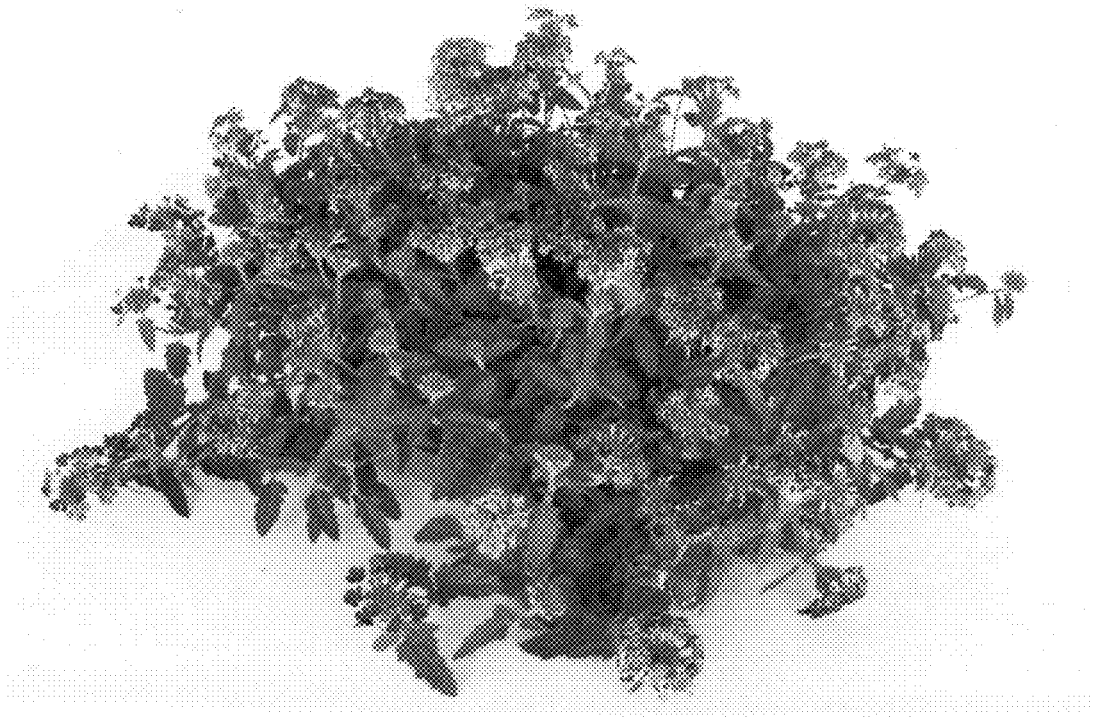

* * * * *